US008091550B2

(12) United States Patent
Steindorf

(10) Patent No.: US 8,091,550 B2
(45) Date of Patent: Jan. 10, 2012

(54) FACE MASK HAVING BAFFLE LAYER FOR IMPROVED FLUID RESISTANCE

(75) Inventor: Eric C. Steindorf, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 905 days.

(21) Appl. No.: 10/743,260

(22) Filed: Dec. 22, 2003

(65) Prior Publication Data

US 2005/0133036 A1 Jun. 23, 2005

(51) Int. Cl.

| | |
|---|---|
| ***A62B 7/10*** | (2006.01) |
| ***A62B 18/02*** | (2006.01) |
| ***A62B 18/08*** | (2006.01) |
| ***A61B 19/00*** | (2006.01) |

(52) U.S. Cl. ......... 128/206.12; 128/205.27; 128/205.29; 128/206.16; 128/206.19; 128/206.21; 128/206.22; 128/863

(58) Field of Classification Search ............. 128/205.27, 128/205.29, 206.16, 206.19, 206.21, 206.22, 128/863

See application file for complete search history.

(56) References Cited

U.S. PATENT DOCUMENTS

| | | | | |
|---|---|---|---|---|
| 3,490,447 | A * | 1/1970 | Jackson | 128/863 |
| 3,929,135 | A | 12/1975 | Thompson | |
| 3,953,566 | A | 4/1976 | Gore | |
| 4,100,324 | A | 7/1978 | Anderson et al. | |
| 4,187,390 | A | 2/1980 | Gore | |
| 4,215,682 | A | 8/1980 | Kubik et al. | |
| 4,374,888 | A | 2/1983 | Bornslaeger | |
| 4,375,718 | A | 3/1983 | Wadsworth et al. | |
| 4,592,815 | A | 6/1986 | Nakao | |
| 4,802,473 | A | 2/1989 | Hubbard et al. | |
| 4,874,659 | A | 10/1989 | Ando et al. | |
| 4,920,960 | A | 5/1990 | Hubbard et al. | |
| 4,951,664 | A * | 8/1990 | Niemeyer | 128/206.24 |
| 4,969,457 | A * | 11/1990 | Hubbard et al. | 128/206.12 |
| 5,020,533 | A | 6/1991 | Hubbard et al. | |
| 5,322,061 | A | 6/1994 | Brunson | |
| 5,383,450 | A | 1/1995 | Hubbard et al. | |

(Continued)

FOREIGN PATENT DOCUMENTS

DE 29815881 U1 1/2000

(Continued)

OTHER PUBLICATIONS

U.S. Appl. No. 10/281,512, filed Oct. 25, 2002.

(Continued)

*Primary Examiner* — Patricia Bianco
*Assistant Examiner* — Nihir Patel
(74) *Attorney, Agent, or Firm* — Dority & Manning, P.A.

(57) ABSTRACT

A face mask is provided. The face mask includes a body portion that is configured to be placed over a mouth and at least part of a nose of a user such that the air of respiration is drawn through the body portion. The body portion includes a baffle layer which helps prevent penetration from a fluid striking the mask. The baffle layer has an outer and an inner surface with a plurality of projections extending from one of the outer or inner surfaces. The baffle layer aids in absorbing energy associated with fluid striking the body portion of the mask. The baffle layer distributes fluid away form the point of impact in the channels between the projections.

26 Claims, 5 Drawing Sheets

U.S. PATENT DOCUMENTS

| | | | | |
|---|---|---|---|---|
| 5,401,446 | A | 3/1995 | Tsai et al. | |
| 5,467,765 | A | 11/1995 | Maturaporn | |
| 5,493,753 | A | 2/1996 | Rostamo | |
| 5,540,976 | A | 7/1996 | Shawver et al. | |
| 5,553,608 | A | 9/1996 | Reese et al. | |
| 5,620,785 | A | 4/1997 | Watt et al. | |
| 5,645,057 | A | 7/1997 | Watt et al. | |
| 5,681,645 | A | 10/1997 | Strack et al. | |
| 5,694,925 | A | 12/1997 | Reese et al. | |
| 5,699,791 | A | 12/1997 | Sukiennik et al. | |
| 5,706,804 | A | 1/1998 | Baumann et al. | |
| 5,724,964 | A | 3/1998 | Brunson et al. | |
| 5,813,398 | A | 9/1998 | Baird et al. | |
| 5,883,026 | A | 3/1999 | Reader et al. | |
| 6,055,982 | A | 5/2000 | Brunson et al. | |
| 6,102,039 | A * | 8/2000 | Springett et al. | 128/206.12 |
| 6,145,504 | A | 11/2000 | Miyake | |
| 6,234,171 | B1 * | 5/2001 | Springett et al. | 128/206.12 |
| 6,354,296 | B1 * | 3/2002 | Baumann et al. | 128/206.19 |
| 6,484,722 | B2 | 11/2002 | Bostock et al. | |
| 2002/0046754 | A1 | 4/2002 | Baumann et al. | |

FOREIGN PATENT DOCUMENTS

| | | | |
|---|---|---|---|
| EP | 0121299 | A2 | 10/1984 |
| EP | 0121299 | A3 | 10/1984 |
| EP | 0391725 | B1 | 6/1994 |
| EP | 0695774 | A2 | 2/1996 |
| EP | 0695774 | A3 | 2/1996 |
| EP | 0929240 | B1 | 10/2002 |
| WO | WO 8101019 | A1 | 4/1981 |

OTHER PUBLICATIONS

U.S. Appl. No. 10/281,511, filed Oct. 25, 2002.

Search Report and Written Opinion for PCT/US2004/020695, dated Jun. 25, 2004.

* cited by examiner

FACE MASK HAVING BAFFLE LAYER FOR IMPROVED FLUID RESISTANCE

BACKGROUND

Face masks and respirators find utility in a variety of manufacturing, custodial, and household applications by protecting the wearer from inhaling dust and other harmful airborne contaminates through their mouth or nose. Likewise, the use of face masks is a recommended practice in the healthcare industry to help prevent the spread of disease. Face masks worn by healthcare providers help reduce infections in patients by filtering the air exhaled from the wearer thus reducing the number of harmful organisms or other contaminants released into the environment.

This is especially important during surgeries where the patient is much more susceptible to infection due to the open wound site. Similarly, patients with respiratory infections may use face masks to prevent the spread of disease by filtering and containing any expelled germs. Additionally, face masks protect the healthcare worker by filtering airborne contaminants and microorganisms from the inhaled air.

Some diseases, such as hepatitis and AIDS, can be spread through contact of infected blood or other body fluids to another person's mucous membranes, ie. eyes, nose, mouth, etc. The healthcare industry recommends specific practices to reduce the likelihood of contact with contaminated body fluids. One such practice is to use face masks which are resistant to penetration from a splash of body fluids.

The section of the face mask that covers the nose and mouth is typically known as the front panel or body portion. The body of the mask can be comprised of several layers of material. At least one layer is composed of a filtration material (filtration media layer) that prevents the passage of germs and other contaminants therethrough but allows for the passage of air so that the user may comfortably breathe. The porosity of the mask refers to how easily air is drawn through the mask. A more porous mask is easier to breathe through. The body portion may also contain multiple layers to provide additional functionality or attributes to the face mask. For example, many face masks include a layer of material on either side of the filtration media layer. The layer that contacts the face of the wearer is typically referred to as the inner facing. The layer furthest from the face is referred to as the outer facing.

Face masks have also been designed to seal around the perimeter of the mask to the face of the wearer. Such a sealing arrangement is intended to force all exchanges of air through the body of the mask in order to prevent airborne pathogens and/or infectious fluids from being transferred to and/or from the wearer.

Attached to the body section are devices to hold the body section securely to the head of the user. For instance, manual tie straps that extend around the user's head and are tied at the back of the wearer's head are typically used in masks worn in surgeries. Respirators used for healthcare typically employ elastic bands that wrap around the head and hold the body section firmly to the face to ensure a tight seal. Masks that use loops that wrap around the wearer's ears are typically used in non-surgical healthcare situations such as isolation wards or by dental hygienists.

As stated, face masks may be designed to be resistant to penetration by splashes of fluids so that pathogens found in blood or other fluids are not able to be transferred to the nose, mouth, and/or skin of the user of the face mask. The American Society of Testing and Materials has developed test method F-1862, "Standard Test Method of Resistance of Medical Face Masks to Penetration by Synthetic Blood (Horizontal Projection of Fixed Volume at a Known Velocity) to assess a face mask's ability to resist penetration by a splash. The splash resistance of a face mask is typically a function of the ability of the layer or layers of the face mask to resist fluid penetration, and/or their ability to reduce the transfer of the energy of the fluid splash to subsequent layers, and/or by their ability to absorb the energy of the splash. Typical approaches to improving fluid resistance are to use thicker materials or additional layers in the construction of the face mask. However, these solutions may increase the cost of the face mask and reduce the porosity of the face mask.

An additional approach to improving the splash resistance of face masks is to incorporate a layer of porous, high loft, fibrous material. This type of material is advantageous in that the layer will absorb the energy of the impact of the fluid splash. However, it is often the case that fluid will saturate this high loft material, hence reducing its effectiveness in absorbing the energy of a future fluid splash. Additionally, fluid can be squeezed out of this high loft material and may be transferred through subsequent layers upon compression of the face mask.

A perforated film incorporated into a face mask is shown in U.S. Pat. No. 4,920,960 (incorporated herein in its entirety for all purposes) may be used in order to provide a fluid barrier to the face mask while still allowing for the user to be able to breath through the perforations in the film.

In some face masks, a layer of point bonded polyolefin, typically a polypropylene spunbond, may be positioned on either side of a filtration media layer to improve splash resistance.

The present invention provides an additional approach to imparting splash resistance to a face mask.

SUMMARY

Various features and advantages of the invention will be set forth in part in the following description, or may be obvious from the description.

The present invention provides for a face mask that includes a body portion configured to be placed over the mouth and at least part of the nose of a user such that the air of respiration is drawn through the body of the mask. The body portion has a baffle layer which dissipates energy of the impact of the splash and/or allows the fluid of the splash to more easily flow laterally away from the site of impact. The baffle layer has an outer and an inner surface. The baffle layer contains a plurality of projections or peaks extending from one or both of the outer or inner surfaces. The baffle layer may be three-dimensionally shaped and contact prior and/or subsequent layers at discrete points. The baffle layer is configured in order to aid in absorbing energy associated with fluid striking the body portion. The baffle layer may constitute the sole layer of the body portion, or may be used in combination with one or more additional layers. For instance, the body portion may have an outer facing which contacts the projections of the baffle layer, and a third layer which contacts the inner surface of the baffle layer.

Other exemplary embodiments of the present invention exist in a face mask as described above where the projections on the outer surface of the baffle layer define a plurality of inter-connected channels for redirecting the flow of fluid that strikes the body portion. In this regard, fluid is directed laterally across the outer surface of the baffle layer away from the point of initial contact of the fluid with the baffle layer.

Alternatively, the baffle layer may not be a separate layer of the body portion, but may instead be incorporated into an existing layer of the body portion. For example, the body portion may have an inner facing layer which contacts the skin of the user, an outer facing layer, and a filtration media layer formed into a three dimensional waffle or egg-carton shape and disposed between the inner facing layer and the outer facing layer. The plurality of projections, which extend from the baffle-media layer, extend from both the inner and outer facings, thus minimizing the contact between the three layers.

The projections on the baffle layer may be in a variety of shapes such as circular pillows, hexagonal cones, circular cones or pleats in accordance with other exemplary embodiments. Further still, the layer having the projections may be a film, and the projections may each include a hole through the film.

An exemplary embodiment of a face mask as described above may include an additional layer in the body portion positioned further away from the user when the face mask is worn and which is stiffer than the baffle layer.

The projections may be located on the outer surface of the baffle layer facing away from the user. Each of the projections defines a cavity on the inner surface of the layer. The body portion of the face mask may have a plurality of layers, and the projections define an interior space between the side of the baffle layer having the projections and an adjacent layer. The cavities on the inner surface of the baffle layer minimize contact between the inner surface of the layer and an adjacent layer, and act to minimize contact between the layers of the face mask in order to help prevent fluid strike through.

The projections and the outer surface of the baffle layer define a plurality of inter-connected channels for redirecting the flow of fluid that strikes the body portion. As such, the fluid may be redirected to portions of the face mask that are more impervious to fluid strike through than the portions that were initially contacted by the fluid. Also, by redistributing the fluid throughout the face mask, fluid is less likely to strike through the face mask since areas of fluid concentration will be either reduced or eliminated. The channels also provide for spacing between adjacent layers of the face mask. This spacing reduces the amount of contact between adjacent layers of the face mask and consequently eliminates or reduces the amount of fluid strike through.

Definitions

As used herein, the term "nonwoven fabric or web" means a web having a structure of individual fibers or threads which are interlaid, but not in an identifiable manner as in a knitted fabric. Nonwoven fabrics or webs have been formed from various processes such as, for example, meltblowing processes, spunbonding processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91).

As used herein, the term "composite" refers to a material which may be a multicomponent material or a multilayer material. These materials may include, for example, stretch bonded laminates, neck bonded laminates, or any combination thereof.

As used herein, the term "ultrasonic bonding" refers to a process in which materials (fibers, webs, films, etc.) are joined by passing the materials between a sonic horn and anvil roll. An example of such a process is illustrated in U.S. Pat. No. 4,374,888 to Bornslaeger, the content of which is incorporated herein by reference in its entirety.

As used herein, the term "thermal point bonding" involves passing materials (fibers, webs, films, etc.) to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. Typically, the percent bonding area varies from around 10 percent to around 30 percent of the area of the fabric laminate. The bonded areas are typically discrete points or shapes and not interconnected. As is well known in the art, thermal point bonding holds the laminate layers together and imparts integrity to each individual layer by bonding filaments and/or fibers within each layer and limiting their movement.

As used herein, the term "thermal pattern bonding" involves passing materials (fibers, webs, films, etc.) to be bonded between a heated calender roll and an anvil roll as with thermal point bonding. The difference is that the bonded areas are interconnected producing discrete areas of unbonded fibers. Various patterns for calender rolls have been developed for functional as well as aesthetic reasons. Typically, the percent bonding area varies from around 10 percent to around 30 percent of the area of the fabric laminate.

As used herein, the term "electret" or "electret treating" refers to a treatment that imparts a charge to a dielectric material, such as a polyolefin. The charge includes layers of positive or negative charges trapped at or near the surface of the polymer, or charge clouds stored in the bulk of the polymer. The charge also includes polarization charges which are frozen in alignment of the dipoles of the molecules. Methods of subjecting a material to electret treating are well known by those skilled in the art. These methods include, for example, thermal, liquid-contact, electron beam, and corona discharge methods. One particular technique of subjecting a material to electret treating is disclosed in U.S. Pat. No. 5,401,466, the contents of which is herein incorporated in its entirety by reference. This technique involves subjecting a material to a pair of electrical fields wherein the electrical fields have opposite polarities.

As used herein, any given range is intended to include any and all lesser included ranges. For example, a range of from 45-90 would also include 50-90; 45-80; 46-89; and the like.

DETAILED DESCRIPTION

Figure 1:
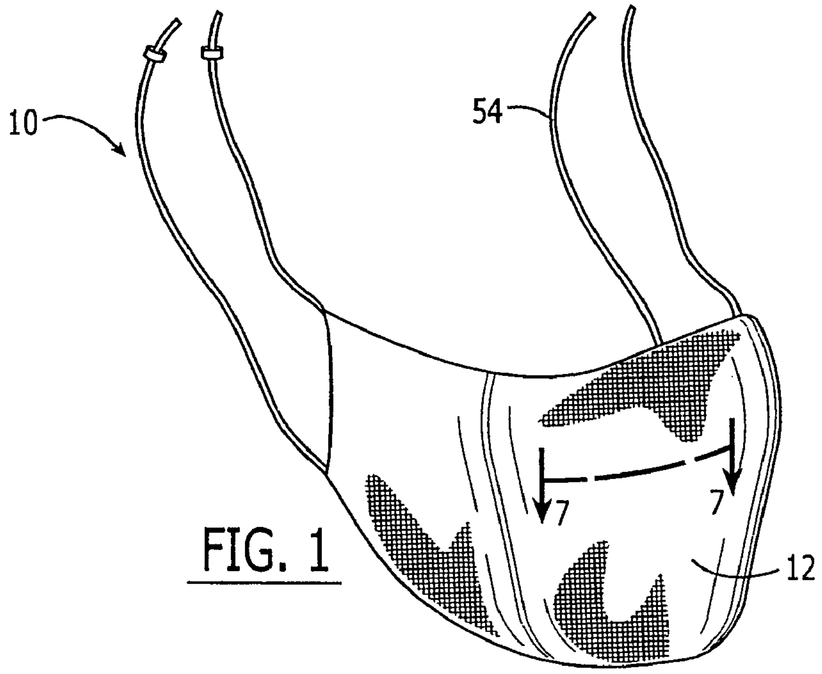
FIG. 1 is a perspective view of a face mask having a body portion.

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

The present invention is not limited to the numerical ranges and limits discussed herein. For example, a range of from about 100 to about 200 also includes ranges from about 110 to about 190, about 140 to about 160, and from 31 to 45. As a further example, a numerical limit of less than about 10 also includes a numerical limit of from less than about 7, less than about 5, and less than about 3.

The present invention provides for a face mask which incorporates a baffle layer. The baffle layer may either be a separate layer of the face mask, or may be incorporated into an already existing layer of the face mask. The baffle layer improves the ability of a face mask to resist penetration by a splash of fluid by reducing the contact of adjacent layers of material and/or absorbing the energy produced by a fluid impact on the face mask, and/or providing for a mechanism by which fluid that strikes the face mask may be channeled away from the point of contact.

Figure 2:
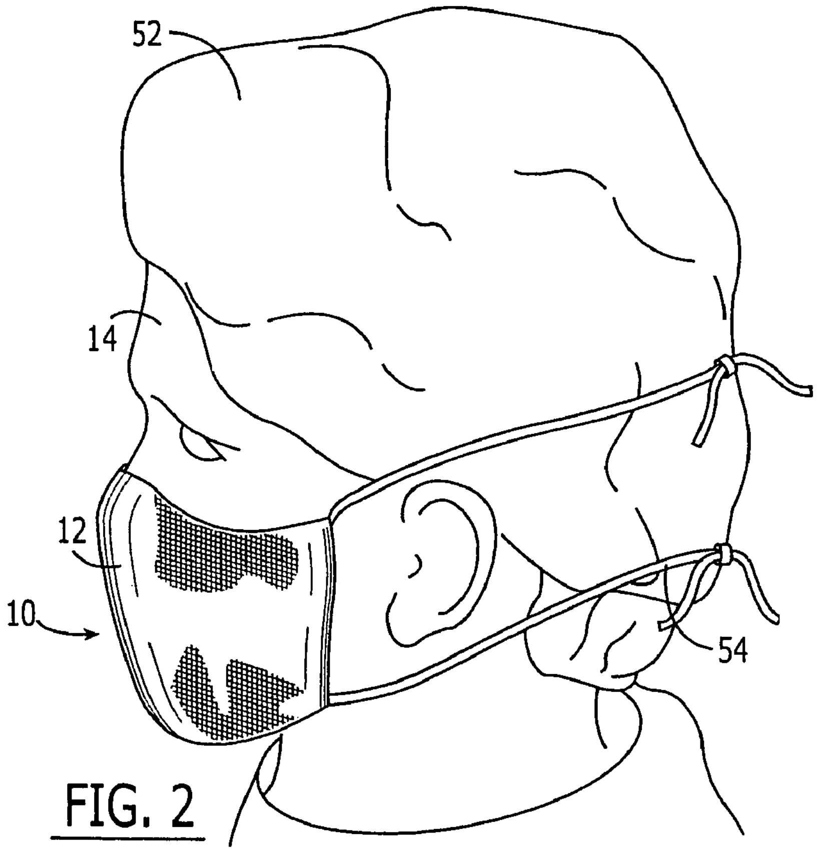
FIG. 2 is a perspective view of a face mask with a body portion. The face mask is attached to the head of a user.

FIGS. 1 and 2 show a face mask 10 which may be used in accordance with one exemplary embodiment of the present invention. The face mask 10 includes a body portion 12 that is configured to be placed over the mouth and at least part of the nose of the user 14 such that the air exchanged through normal respiration passes through the body portion 12 of the face mask 10. It is to be understood, however, that the body portion 12 can be of a variety of styles and geometries, such as, but not limited to, flat half mask, pleated face masks, cone masks, flat folded personal respiratory devices, duckbill style mask, trapezoidally shaped masks, etc. The body portion 12 may be configured as that shown in U.S. Pat. No. 6,484,722 which is incorporated by reference herein in its entirety for all purposes. The face mask 10 therefore isolates the mouth and the nose of the user 12 from the environment. The face mask 10 is attached to the user 14 by a pair of tie straps 54 which are wrapped around the head of the user 14 (and a hair cap 52 if worn by the user) and are connected to one another. It is to be understood, however, that other types of fastening arrangements may be employed in accordance with various exemplary embodiments of the present invention. For instance, instead of the tie straps 54, the face mask 10 may be attached to the user 14 by ear loops, elastic bands wrapping around the head, a hook and loop type fastener arrangement, wrapped as a single piece around the head of the user 14 by an elastic band, or may be directly attached to the hair cap 52.

Additionally, the configuration of the face mask 10 may be different in accordance with various exemplary embodiments. In this regard, the face mask 10 may be made such that it covers both the eyes, hair, nose, throat, and mouth of the user. As such, the present invention is not limited to only face masks 10 that cover only the nose and mouth of the user 14.

Figure 3:
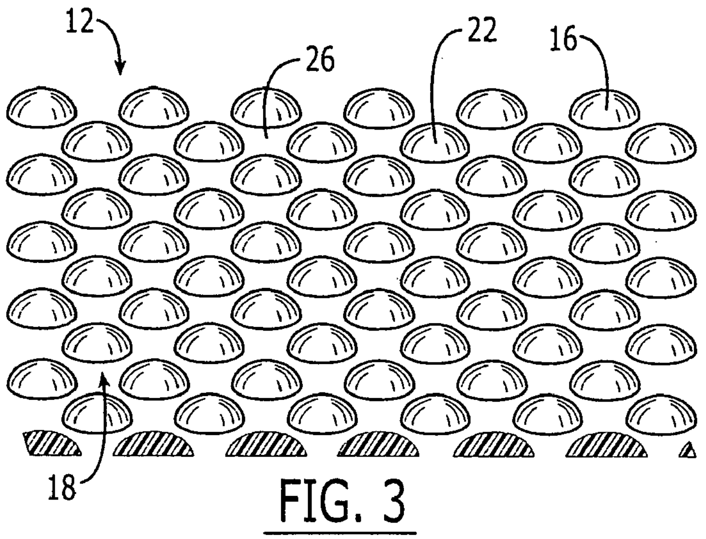
FIG. 3 is a perspective view of a layer of the face mask, which may be a baffle layer, that has a plurality of projections. In this exemplary embodiment of the present invention, the projections are circular pillows.

The present invention provides for a baffle layer 16 incorporated in the body portion 12 of the face mask 10, one exemplary embodiment of which is shown in FIG. 3. Here, the baffle layer 16 has a three dimensional shape such that the outer surface 18 of the baffle layer 16 has a plurality of projections 22 extending therefrom. As shown in FIG. 3, the projections 22 are all substantially uniform, and are circular pillows. The baffle layer 16 in this instance may be a high loft bicomponent spunbond material. The circular pillow shaped projections 22 may be formed by thermal pattern bonding the baffle layer 16.

Figure 7:
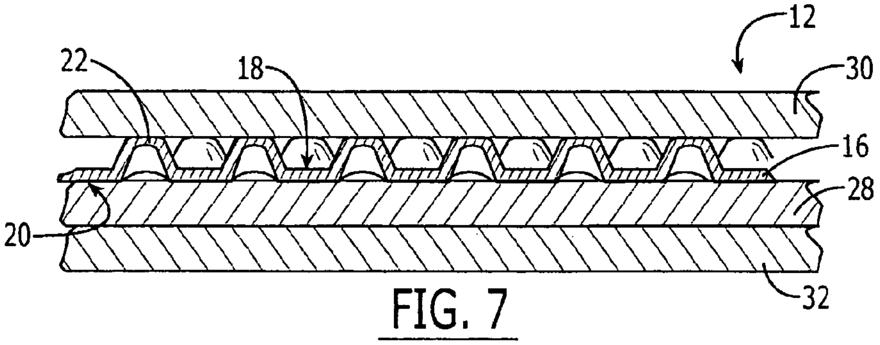
FIG. 7 is a cross-sectional view taken along line 7-7 of FIG. 1.

FIG. 7 is a cross-sectional view taken along line 7-7 of FIG. 1, and shows the baffle layer 16 of FIG. 3 incorporated into the face mask 10. In this exemplary embodiment, the body portion 12 of the face mask 10 includes four layers. The baffle layer 16 is a separate layer in the body portion 12, and is disposed between the outer facing 30 and the filtration media layer 28. An inner facing layer 32 is disposed adjacent the filtration media layer 28.

The inner facing layer 32 contacts the skin of the user 14 (FIG. 2) of the face mask 10. The outer facing 30 is the portion of the body portion 12 located furthest away from the user 14 (FIG. 2) when the face mask 10 is worn. The filtration media layer 28 is configured to prevent the passage of pathogens through the body portion 12, but still allow for the passage of air in order to permit the user 14 (FIG. 2) to breath. As can be imagined, the arrangement of the layers 16, 28, 30 and 32 within the body portion 12 may be modified such that any combination of sequencing is possible. For instance, the first layer 28, which may be a filtration media layer, may be located on the outer most or inner most portion of the body portion 12.

Figure 9:
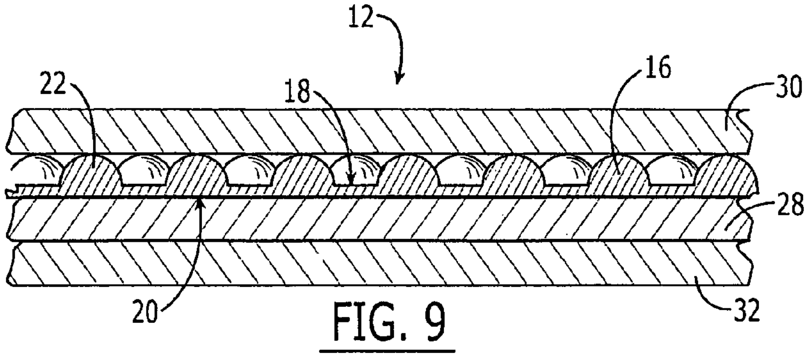
FIG. 9 is a partial cross-sectional view of an exemplary embodiment of a face mask in accordance with the present invention. Here, fluid layers are present in the body portion, and the baffle layer is disposed between a first and second layer of the body portion.

With reference to FIGS. 3 and 9, it can be seen that the projections 22 extend from the outer surface 20 of the baffle layer 16 and are oriented away from the filtration media layer 28. In this regard, fluid which strikes the outer facing layer 30 of the body portion 12, imparts a force onto the body portion 12 that is transferred through the outer facing 30 and into the projections 22.

The projections 22 are configured such that their three dimensional structure absorbs at least a portion of the forces transmitted by the fluid striking the outer facing 30 of the body portion 12. Absorption of these forces imparted by a fluid strike may help to prevent fluid from penetrating the filtration media layer 28 and the inner facing 32 of the body portion 12. In this regard, it may be the case that fluid is already trapped between one or more layers of the body portion 12. Forces imparted by the fluid striking the body portion 12 may cause these already trapped fluids to be pushed further through the body portion 12. By having the baffle layer 16 absorb either all of part of the forces produced by a fluid strike on the body portion 12, the baffle layer 16 will help to prevent these trapped fluids from propagating through the layers of the body portion 12, and contacting the user 14 (FIG. 2) of the face mask 10.

Figure 11:
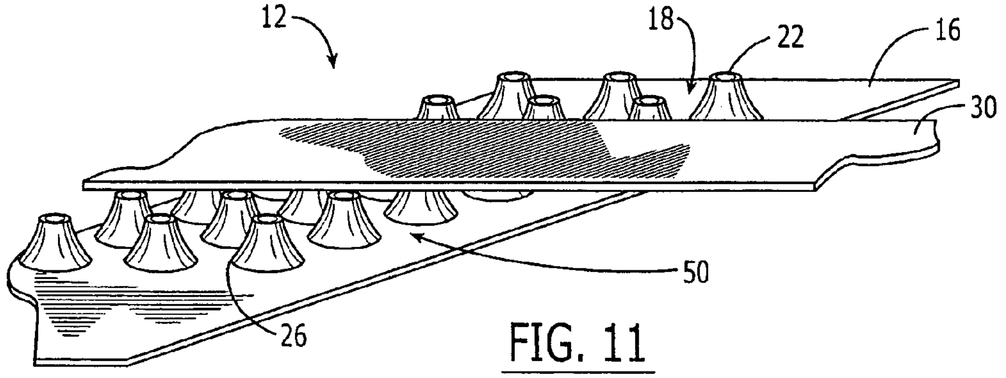
FIG. 11 is a partial perspective view of an exemplary embodiment of the face mask in accordance with the present invention. Here, the projections on the outer surface of the baffle layer define an interior space between the outer surface of the baffle layer and the layer adjacent to the baffle layer which contacts the projections of the baffle layer.
Figure 12:
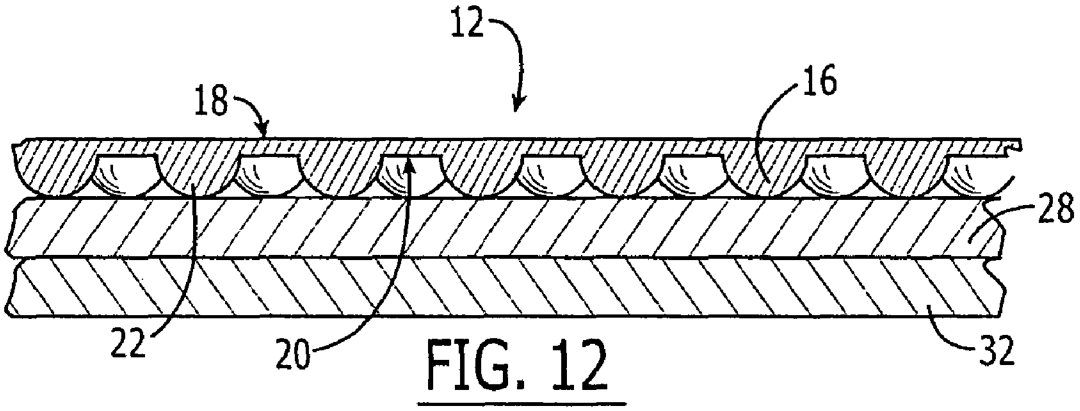
FIG. 12 is a partial cross-sectional view of an exemplary embodiment of a face mask in accordance with the present invention. Here, the baffle layer is disposed as the outer facing of the body portion. The outer surface of the baffle layer is flat, and protrusions extend from the inner surface of the baffle layer to contact the filtration media layer.

As can been seen in FIG. 7, the projections 22 define channels 26 that are located on the outer surface 20 of the baffle layer 16. As can be seen more clearly in FIG. 11, the projections 22 define an interior space 50 between the baffle layer 16 and the outer facing layer 30. Likewise, the cavities 48 also define spaces between the inner surface 18 of the baffle layer 16 and the filtration media layer 28. The interior space 50 (FIG. 11) and the spaces formed by the cavities 48 causes the layers 30 and 28 to be separated. This helps to reduce the area of contact between the layers and thus lowers the ability of fluid to wick from one layer to the next. As such, the protrusions 22 therefore help to separate the layers of the body portion 12 such that fluid cannot be as easily transferred through the layers of the body portion 12 by decreasing the area of surface contact between the layers.

Figure 8:
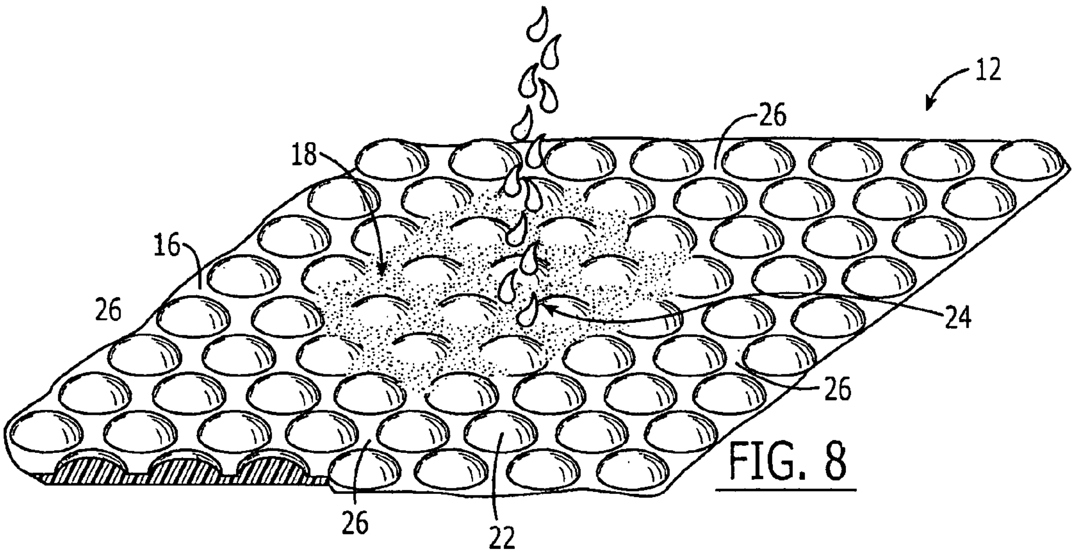
FIG. 8 is a perspective view of a layer, which may be a baffle layer, in accordance with one exemplary embodiment of the present invention. Fluid is shown striking the baffle layer and being redirected away via a plurality of channels which are defined on the baffle layer.

FIG. 8 shows a perspective view of the baffle layer 16 used in FIGS. 3 and 7. As can be seen in FIG. 8, the projections 22 define a plurality of channels 26 on the outer surface 18 of the baffle layer 16. Fluid which strikes the baffle layer 16 directly, or is transferred to the baffle layer 16 through a preceding layer of the body portion 12, contacts the baffle layer 16 at a point of contact 24. Fluid may then be dispersed from the point of contact 24 by being transferred through the channels 26 on the outer surface 18 of the baffle layer 16. By providing the channels 26, the fluid may be transferred and more uniformly distributed across the outer surface 18 of the baffle layer 16.

This distribution of fluid helps to prevent the accumulation of a pool of fluid at a particular location on the outer surface 18 of the baffle layer 16. It is typically the case that fluid which is heavily concentrated at a particular location on the baffle layer 16 is more likely to be transferred through the baffle layer 16, as opposed to the situation in which the same amount of fluid were distributed over a larger portion of the outer surface 18 of the baffle layer 16.

The channels 26 may be interconnected channels such that all of the channels 26 are in communication with one another. This allows for the advantage of having fluid which contacts the baffle layer 16 at any point of contact 24 to be distributed through a larger number of channels 26. Alternatively, the channels 26 may be configured such that only a portion of the channels 26 are in communication with one another. Further, the channels 26 may be provided in any number in accordance with other exemplary embodiments of the present invention.

The channels 26 may thus redirect fluid which contacts the baffle layer 16 to a desired location on or in the body portion 12. For instance, the channels 26 may be configured such that fluid which engages the baffle layer 16 at the point of contact 24 is redirected along the outer surface 18 of the baffle layer and flows through the body portion 12 to a position along, for instance, the sides of the face mask 10. This type of an arrangement may be advantageous in that fluid is prevented from contacting the nose and/or mouth of the user of the face mask 10, and is instead redirected to locations away from the nose and/or mouth of the user.

As shown in FIG. 7, the baffle layer 16 may be one layer out of four layers that compose the body portion 12 of the face mask 10. However, it is to be understood that, in accordance with various exemplary embodiments of the present invention, any number of layers may compose the body portion 12. For instance, in accordance with one exemplary embodiment of the present invention, only a single layer, that being the baffle layer 16, is used to compose the body portion 12. Alternatively, the body portion 12 may be configured such that the baffle layer 16 does not have a layer immediately adjacent thereto on either side of the baffle layer 16. In this regard, it may be the case that the inner surface 20 of the baffle layer 16 directly contacts the skin of the user. Alternatively, the body portion 12 may be configured such that the outer surface 18 of the baffle layer 16 defines the outer most portion of the body portion 12 such that the outer layer 18 of the baffle layer 16 essentially composes the outer surface of the face mask 10. In this embodiment, if the baffle layer 16 has protrusions 22 from only one surface, the splash resistance would be optimized by having the peaks on the inner surface 20 of the baffle layer 16. This would minimize the contact between the baffle layer 16 and the adjacent layer. As such, it is the case that the present invention includes various exemplary embodiments in which layers are not present on either side of the baffle layer 16.

In accordance with one exemplary embodiment of the present invention, the body portion 12 is configured such that the baffle layer 16 has a layer adjacent to both the outer and inner surfaces 18, 20 of the baffle layer 16. Additionally, the layer from which the force of impact from a fluid strike is transferred to the baffle layer 16 may be constructed so that this layer is stiffer than the baffle layer 16. For example, referring to FIG. 7, the fluid may contact the outer facing 30. Fluid penetrating the outer facing 30 would collect in the channels 26 between the peaks 22 of the baffle layer 16. applicant has discovered that by making one or more layers that are in front of the baffle layer 16, in regards to a fluid strike, stiffer than the baffle layer 16, an advantage is realized in that energy of the impact of a fluid strike is distributed over a wider area of the body portion 12. In this regards, it is less likely for fluid to be transferred through the body portion 12. However, the present invention also includes exemplary embodiments in which the baffle layer is stiffer than, or as stiff as, preceding layers.

Figure 10:
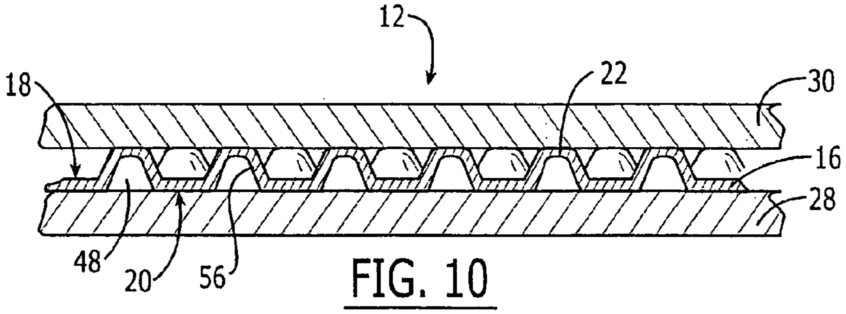
FIG. 10 is a partial cross-sectional view of an exemplary embodiment of a face mask in accordance with the present invention. In this exemplary embodiment, a baffle layer, which may be also a filtration media layer, is disposed between an inner facing layer and an outer facing layer.

FIG. 10 shows such an example in which the baffle layer 16 is incorporated into the filtration media layer 28 of the body portion 12. As can be seen, a first layer which may be an outer facing layer is disposed adjacent to the outer surface 18 of the baffle layer 16, and a second layer, which may be an inner facing layer, is disposed adjacent the inner surface 20 of the baffle layer 16. Alternatively, the baffle layer 16 may be incorporated into the face mask 10 such that the baffle layer 16 is incorporated into the outer facing 30 or the inner facing 32 of the body portion 12.

Additional exemplary embodiments of the present invention exist in which more that one baffle layer 16 may be incorporated into the body portion 12. For instance, baffle layers 16 may be incorporated into the body portion 12, in which the filtration media layer 28 has been formed into a three dimensional baffle layer shape. Still further exemplary embodiments of the present invention exist in which the baffle layer 16 may be oriented such that the projections 22 extend towards the user. Referring to FIG. 10, the baffle layer 16 may be flipped upside down such that the projections 22 extend towards the inner facing 32, and consequently towards the user 14 (FIG. 2) of the face mask 10. Still further exemplary embodiments of the present invention exist in which the projections 22 may extend both towards and away from the user. In this regard, it may be the case that the projections 22 cushion the force of the impact of a fluid strike better at certain locations on the body portion 12 if the projections 22 extend towards the user. As such, the present invention is not limited to having the projections 22 extend away from the user when the face mask 10 is worn.

FIG. 9 shows an alternative exemplary embodiment in which the baffle layer 16 has a plurality of projections 22 extending from an outer surface 20 thereof. However, unlike previously discussed exemplary embodiments, the projections 22 do not define a plurality of cavities on the inner surface 18 of the baffle layer 16. In this regard, the inner surface 18 of the baffle layer 16 contacts the filtration media layer 28 of the body portion 12 essentially along the entire surface of the inner surface 18. In yet another exemplary embodiment, additional projections 22 may extend from the inner surface 18 of the baffle layer 16 and engage the filtration media layer 28. In such a configuration, a pair of interior spaces 50 (FIG. 11) would be created, one being defined between the outer surface 20 and the outer facing 30, and the other being defined between the inner surface 18 and the filtration medial layer 28.

Figure 4:
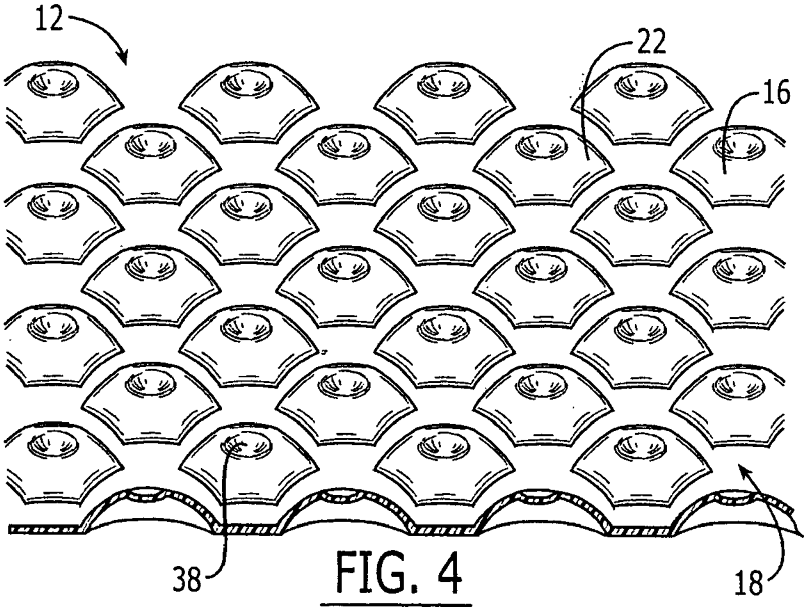
FIG. 4 is a perspective view of an exemplary embodiment of a layer, which may be a baffle layer, of the body portion which has a plurality of projections. In this exemplary embodiment of the present invention, the projections are hexagonal in shape.

Additional exemplary embodiments exist in which the projections 22 are not in the shape of circular pillows. For instance, FIG. 4 shows an embodiment in which the baffle layer 16 is an embossed bonded-carded web material. In this instance, the projections 22 are hexagonal in shape. The baffle layer 16 may be a light weight (0.5 to 1.9 osy) bonded-carded web material in which the hexagonal shaped projections 22 are embossed therein using mated embossing rolls. The projections 22 may still be arranged in order to define a plurality of inter-connected channels 26. A dimple 38 may be located on the outer surface of the hexagonal shaped projections 22. The presence of the dimples 38 may provide for an increased structural rigidity of the baffle layer 16, and may also provide for additional space which further cushions the force of impact of a fluid strike, and minimizes contact with an adjacent layer hence reducing the chances of fluid penetration.

Figure 5:
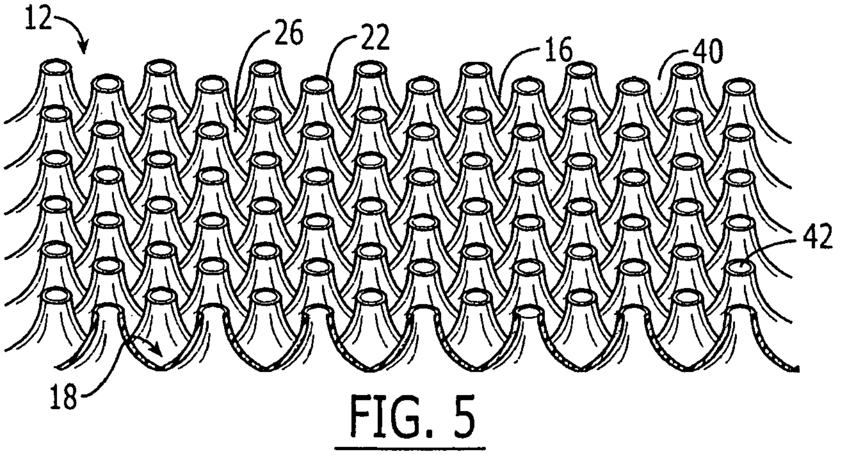
FIG. 5 is a perspective view of a layer, which may be a baffle layer, of the body portion of the face mask. In this exemplary embodiment of the present invention, the layer is a film and has a plurality of projections in which each defines a hole therethrough.

A further exemplary embodiment of the baffle layer 16 is shown in FIG. 5. In this instance, the baffle layer 16 may be formed from a material that is an impervious film 40. The film 40 may be made such that it prevents fluid transfer therethrough, further enhancing the ability of the body portion 12 to prevent fluid strike through. The film 40 may in one exemplary embodiment be Tredegar 6607 Vispore film. An example of a perforated film 40 may be found in U.S. Pat. No. 4,920,960 described above.

The baffle layer 16 shown in FIG. 5 may have a plurality of perforations in the form of holes 42 disposed therethrough. The holes 42 are located on each one of the projections 22. The holes 42 allow for the transfer of air through the baffle layer 16, hence allowing the user to breath. However, should the holes 42 be of too large a size, fluid which accumulates at a particular location on the baffle layer 16 may be transferred through the hole or holes 42. In this instance, an optimal size of the hole 42 may be provided such that it allows for air to be transferred through the baffle layer 16, yet prevents the transfer of fluid therethrough. In accordance with one exemplary embodiment of the present invention, the holes 42 may be 1 millimeter in diameter. Alternatively, the holes 42 may be between 0.5 millimeters and 1.5 millimeters in accordance with various exemplary embodiments.

Figure 6:
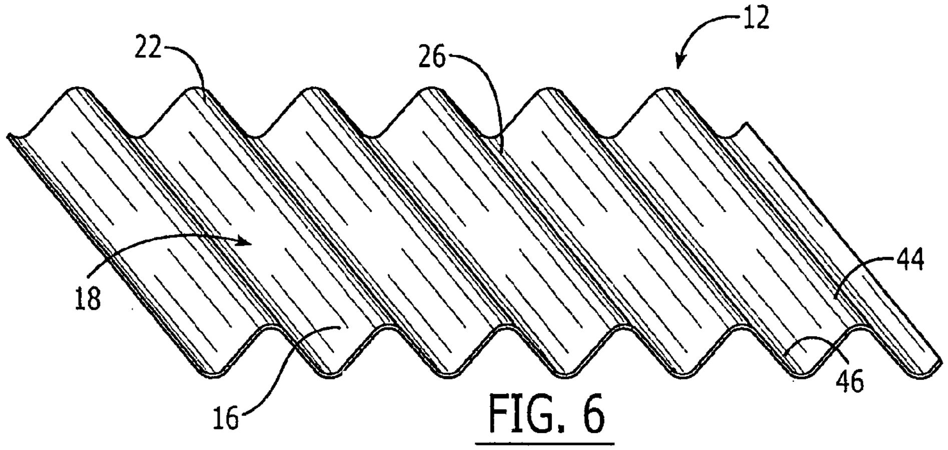
FIG. 6 is a perspective view of a layer, which may be a baffle layer, of the body portion of the face mask. In this exemplary embodiment of the present invention, the layer has a plurality of projections which are a series of ridges that define grooves in the layer such that the layer has a corrugated shape.

FIG. 6 shows an alternative configuration in which the projections 22 are in the form of ridges 44 located along the outer surface 18 of the baffle layer 16. The plurality of ridges 44 define a plurality of valleys 46 therebetween. As such, the outer surface 18 of the baffle layer 16 in this exemplary embodiment has a corrugated shape. Fluid which contacts the baffle layer 16 may be transferred along the valleys 46, which act as the channels 26 as discussed in previous exemplary embodiments. The valleys 46 may be inter-connected with one another, or may be independent from one another in regards to various configurations of the baffle layer 16. Additionally, the ridges 44 may form corresponding cavities on the inner surface 20 of the baffle layer 16, much like the projections 22 form the cavities 48 as discussed above with respect to other exemplary embodiments.

It is therefore the case that the projections 22 may be provided in any of number of styles, shapes, or patterns. Smaller, tighter patterns of the projections may be used in order to provide for support for less stiff outer layers of the body portion 12. Larger, more open patterns of the projections 22 may be used in order to provide for a larger channel volume of the baffle layer 16 in order to collect a greater amount of fluid.

The baffle layer 16 may be made of a hydrophobic material such as a polyolefin non-woven material. Should the face mask 10 be constructed such that the baffle layer 16 is a separate layer, the baffle layer 16 may be made of a material that is porous enough to have a minimum impact on the breathability of the face mask 10, yet closed enough to resist the penetration of the splash brought about by a fluid strike.

The body portion 12 of the face mask 10 may be made of inelastic materials. Alternatively, the material used to construct the body portion 12 may be comprised of elastic materials, allowing for the body portion 12 to be stretched over the nose, mouth, and/or face of the user 14 (FIG. 2).

Although not shown in the drawings, structural elements may be incorporated into the body portion 12 in order to provide for a face mask 10 with different desired characteristics. For instance, a series of stays may be employed within the body portion 12. The stays may provide for structural rigidity of the body portion 12, and may also be shaped in order to help seal the periphery of the body portion 12. Alternatively, a stay may be employed within the body portion 12 in order to help conform the body portion 12 around the nose of the user.

Additionally, a stay may be employed in order to better shape the body portion 12 around the chin of the user. The stays may allow for a better fit of the body portion 12 and may allow for the construction of a cavity around the mouth and/or nose of the user. However, it is to be understood that in other exemplary embodiments of the present invention, the body portion 12 may be provided with any number of, or no stays. A series of stays incorporated into a face mask 10 is disclosed in U.S. Pat. No. 5,699,791, the contents of which are incorporated herein by reference in their entirety for all purposes. Stays may be made of an elongated malleable member such as a metal wire or an aluminum band that can be formed into a rigid shape in order to impart this shape into the body portion 12 of the face mask 10.

The baffle layer 16 disclosed in the present invention may be incorporated into any face mask style or configuration, including rectangular masks, pleated masks, duck bill masks, cone masks, trapezoidal masks, etc. The face mask 10 according to the present invention may also incorporate any combination of known face mask 10 features, such as visors or shields, anti-fog tapes, sealing films, beard covers, etc. Exemplary faces masks are described and shown, for example, in the following U.S. patents: U.S. Pat. Nos. 4,802,473; 4,969, 457; 5,322,061; 5,383,450; 5,553,608; 5,020,533; and 5,813,398. These patents are incorporated herein in their entirety by reference for all purposes.

As stated, the mask face 10 may be composed of layers 16, 28, 30, and 32. These layers may be constructed from various materials known to those skilled in the art. For instance, the outer facing 30 of the body portion 12 may be any nonwoven web, such as a spunbonded, meltblown, or coform nonwoven web, a bonded carded web, or a wetlaid composite. The inner facing 32 of the body portion 12 and outer facing 30 may be a necked nonwoven web or a reversibly necked nonwoven web. The inner facing 32 and the outer facing 30 may be made of the same materials or different materials.

Many polyolefins are available for nonwoven web production, for example polyethylenes such as Dow Chemical's ASPUN® 6811A linear polyethylene, 2553 LLDPE and 25355, and 12350 polyethylene are such suitable polymers. Fiber forming polypropylenes include, for example, Exxon Chemical Company's Escorene® PD 3445 polypropylene and Himont Chemical Co.'s PF-304. Many other suitable polyolefins are commercially available.

The various materials used in construction of the face mask 10 may be a necked nonwoven web, a reversibly necked nonwoven material, a neck bonded laminate, and elastic materials such as an elastic coform material, an elastic meltblown nonwoven web, a plurality of elastic filaments, an elastic film, or a combination thereof. Such elastic materials have been incorporated into composites, for example, in U.S. Pat. No. 5,681,645 to Strack et al., U.S. Pat. No. 5,493,753 to Levy et al., U.S. Pat. No. 4,100,324 to Anderson et al., and in U.S. Pat. No. 5,540,976 to Shawver et al, the contents of which are incorporated herein by reference in their entirety for all purposes. In an exemplary embodiment where an elastic film is used on or in the body portion 12, the film must be sufficiently perforated to ensure that the user can breathe through the body portion 12.

The filtration media layer (layer 28 in FIG. 7) may be a meltblown nonwoven web and, in some embodiments, may be an electret. Electret treatment results in a charge being applied to the filtration media layer which further increases filtration efficiency by drawing particles to be filtered toward the filtration media layer by virtue of their electrical charge. Electret treatment can be carried out by a number of different techniques. One technique is described in U.S. Pat. No. 5,401,446 to Tsai et al. assigned to the University of Tennessee Research Corporation and incorporated herein by reference in its entirety for all purposes. Other methods of electret treatment are known in the art, such as that described in U.S. Pat. No. 4,215,682 to Kubik et al., U.S. Pat. No. 4,375,718 to Wadsworth, U.S. Pat. No. 4,592,815 to Nakao and U.S. Pat. No. 4,874,659 to Ando, the contents of which are incorporated herein by reference in their entirety.

The filtration media layer (layer 28 in FIG. 7) may be made of an expanded polytetrafluoroethylene (PTFE) membrane, such as those manufactured by W. L. Gore & Associates. A more complete description of the construction and operation of such materials can be found in U.S. Pat. No. 3,953,566 to Gore and U.S. Pat. No. 4,187,390 to Gore, the contents of which are incorporated herein by reference in their entirety. The expanded polytetrafluoroethylene membrane may be incorporated into a multi-layer composite, including, but not limited to, an outer nonwoven web layer, an extensible and retractable layer, and an inner layer comprising a nonwoven web.

Multiple layers of the face mask 10 may be joined by various methods, including adhesive bonding, thermal point bonding, or ultrasonic bonding.

It should be understood that the present invention includes various modifications that can be made to the exemplary embodiments of the face mask 10 described herein as come within the scope of the appended claims and their equivalents.

What is claimed is:

1. A face mask, comprising:

a body portion configured to be placed over a mouth and at least part of a nose of a user in order to isolate the mouth and the at least part of the nose of the user from the environment such that the air of respiration is drawn through the body portion, the body portion having a baffle layer configured to cover the user's mouth and at least part of the user's nose and having an outer and an inner surface with a plurality of projections extending from at least one of the outer and inner surfaces that define a plurality of channels on the baffle layer configured for channeling fluid to different locations on the baffle layer, the baffle layer configured to aid in absorbing energy associated with fluid striking the body portion and to prevent fluid strike through.

2. The face mask of claim 1, wherein the channels are interconnected and are defined by the projections and the outer surface of the baffle layer, the channels having an orientation such that the fluid is directed laterally away from the point of impact of the fluid through the channels.

3. The face mask of claim 1, wherein:

the body portion has a first layer contacting the projections of the baffle layer; and the body portion has a third layer contacting the inner surface of the baffle layer.

4. The face mask of claim 3, wherein the first layer is stiffer than the baffle layer.

5. The face mask of claim 1, wherein the projections are circular pillows.

6. The face mask of claim 1, wherein the projections are hexagonal in shape.

7. The face mask of claim 1, wherein the baffle layer is a film, and wherein each of the projections defines a hole therethrough.

8. The face mask of claim 1, wherein the projections are ridges that define a plurality of valleys such that the outer surface of the baffle layer has a corrugated shape.

9. The face mask of claim 1, wherein the plurality of projections each defines a cavity on the inner surface of the baffle layer.

10. The face mask of claim 1, wherein the plurality of projections extend from the outer surface of the baffle layer.

11. The face mask of claim 1, wherein the baffle layer is made from a web formed into a three-dimensional shape.

12. A face mask comprising:

a body portion configured to be placed over a mouth and at least part of a nose of a user in order to isolate the mouth and the at least part of the nose of the user from the environment such that the air of respiration is drawn through the body portion, the body portion having at least one layer configured to cover the user's mouth and at least part of the user's nose, the layer having an outer surface facing away from the user when worn and an inner surface facing towards the user when worn, the layer having a plurality of projections extending therefrom, the projections aiding in absorbing energy associated with fluid striking the body portion, wherein the projections define a plurality of channels on the layer configured for channeling fluid to different locations on the layer.

13. The face mask of claim 12, wherein the body portion has an inner facing layer contacting the skin of the user when worn, an outer facing layer, and a filtration media layer disposed between the inner facing layer and the outer facing layer, wherein the layer with the plurality of projections is any one of the inner facing layer, outer facing layer, and filtration media layer.

14. The face mask of claim 13, wherein the plurality of projections extend from an outer surface of the filtration media layer.

15. The face mask of claim 13, wherein the outer facing layer is stiffer than the filtration media layer.

16. The face mask of claim 12, wherein the body potion has an additional layer that is the layer farthest from the user when worn and adjacent to the layer having the projections, the additional layer stiffer than the layer having the projections.

17. The face mask of claim 12, wherein the body has a plurality of layers, and wherein the projections define an interior space between the layer having the projections and an adjacent layer.

18. The face mask of claim 12, wherein the projections are located on the outer surface of the layer and wherein each of the projections defines a cavity on the inner surface of the layer, and wherein the body portion has a plurality of layers, and wherein the projections define an interior space between the layer having the projections and an outer adjacent layer, and wherein the cavities on the inner surface of the layer minimize contact between the inner surface of the layer and an inner adjacent layer.

19. The face mask of claim 12, wherein the projections and the outer surface of the layer define a plurality of interconnected channels for redirecting the flow of fluid that strikes the body portion such that the fluid is directed across the outer surface of the layer having the projections away from the point of initial contact of the fluid with the layer.

20. The face mask of claim 12, wherein the projections are circular pillows.

21. The face mask of claim 12, wherein the projections are hexagonal in shape.

22. The face mask of claim 12, wherein the layer having the projections is a film, and wherein each of the projections defines a hole therethrough.

23. The face mask of claim 12, wherein the projections are ridges that define a plurality of grooves such that the outer surface of the layer having the projections has a corrugated shape.

24. The face mask of claim 12, wherein the plurality of projections each defines a cavity on the opposite surface of the layer from which the plurality of projections extend.

25. The face mask of claim 12, wherein the plurality of projections extend from the outer surface of the layer having the projections.

26. The face mask of claim 12, wherein the body portion is made from a web formed into a three-dimensional shape.

* * * * *